United States Patent [19]

Clough et al.

[11] Patent Number: 4,882,341
[45] Date of Patent: Nov. 21, 1989

[54] AMINO SUBSTITUTED PROPENOATES AND THEIR USE AS FUNGICIDES

[75] Inventors: John M. Clough, High Wycombe; Ian T. Kay, Wokingham, both of England

[73] Assignee: Imperial Chemical Industries PLC, London, England

[21] Appl. No.: 243,146

[22] Filed: Sep. 9, 1988

Related U.S. Application Data

[63] Continuation of Ser. No. 785,851, Oct. 9, 1985, abandoned.

[30] Foreign Application Priority Data

Oct. 19, 1984 [GB] United Kingdom ................ 8426472
May 23, 1985 [GB] United Kingdom ................ 8513105

[51] Int. Cl.$^4$ .................. A61K 31/44; A61K 31/335; A61K 31/38; A61K 31/21; C07D 213/00; C07D 413/00; C07D 333/22; C07D 307/02; C07C 101/02; C07C 101/44; C07C 69/74; C07C 101/30

[52] U.S. Cl. ..................... 514/332; 514/333; 514/336; 514/344; 514/352; 514/444; 514/447; 514/471; 514/472; 514/530; 514/531; 514/534; 514/535; 514/539; 514/541; 514/543; 514/545; 514/549; 546/256; 546/262; 546/263; 546/283; 546/284; 546/286; 546/287; 546/288; 546/289; 546/297; 546/298; 546/300; 546/301; 546/302; 549/59; 549/60; 549/61; 549/63; 549/64; 549/68; 549/70; 549/71; 549/72; 549/483; 549/484; 549/487; 560/16; 560/37; 560/42; 560/43; 560/116; 560/118; 560/125; 560/147; 560/156; 560/169; 560/170

[58] Field of Search ............... 514/332, 335, 336, 344, 514/352, 444, 447, 471, 472, 530, 531, 534, 535, 539, 541, 543, 545, 549; 560/16, 37, 42, 116, 118, 125, 147, 156, 169, 170, 43; 546/256, 262, 263, 283, 284, 286, 287, 288, 289, 297, 300, 301, 302; 549/59–61, 63–64, 68, 70–72, 483, 484, 487

[56] References Cited

U.S. PATENT DOCUMENTS 4,330,556  5/1982  Hubele et al. ................ 560/43 X
4,420,490 12/1983  Sallmann et al. ............. 560/39 X
4,421,765 12/1983  Sallmann et al. ............. 560/39 X Primary Examiner—Werren B. Lone
Assistant Examiner—Vera C. Clarke
Attorney, Agent, or Firm—Cushman, Darby & Cushman

[57] ABSTRACT

The invention relates to amino substituted propenoates and their use against fungi.

9 Claims, No Drawings

AMINO SUBSTITUTED PROPENOATES AND THEIR USE AS FUNGICIDES

This is a continuation of application Ser. No. 785,851, filed Oct. 9, 1985, which was abandoned upon the filing hereof.

This invention relates to derivatives of acrylic acid useful as fungicides, to processes for preparing them, to fungicidal compositions containing them, and to methods of combating fungi, especially fungal infections in plants, using them.

The invention provides a compound having the general formula (I):

$$R^1-\overset{\overset{X}{\|}}{C}-\underset{\underset{R^2}{|}}{N}-\overset{\overset{CO_2R^3}{|}}{C}=\underset{\underset{OR^4}{|}}{CH} \qquad (I)$$

and stereoisomers thereof, wherein X is an oxygen or a sulphur atom; $R^1$, $R^2$ and $R^3$, which may be the same or different, are hydrogen atoms or alkyl, cycloalkyl, optionally substituted alkenyl, optionally substituted aryl, optionally substituted alkynyl, haloalkyl, optionally substituted aralkyl, or cycloalkylalkyl groups; and $R^4$ can be any of the groups as defined for $R^1$, $R^2$ and $R^3$, except that it is not a hydrogen atom; and metal complexes thereof.

The compounds of the invention contain at least one carbon-carbon double bond, and may be obtained in the form of mixtures of geometric isomers. However, these mixtures can be separated into individual isomers, and this invention embraces such isomers.

Alkyl groups can be in the form of straight or branched chains, and preferably contain 1 to 6 carbon atoms; examples are methyl, ethyl, propyl (n-or iso-propyl) and butyl (n-, sec-, iso-, or t-butyl).

In the preferred compounds of the invention the groups $R^2$, $R^3$ and $R^4$ are each methyl groups and the group $R^1$ is the group $E-R^5CH:CH$ wherein $R^5$ is an optionally substituted aryl, optionally substituted alkenyl, alkyl or cycloalkyl group. In especially preferred compounds of the invention the group $R^1$ is the group $E-R^5CH:CH$ wherein $R^5$ is an optionally substituted phenyl group or an optionally substituted aromatic heterocycle. Examples of suitable substituents for the group $R^5$ when it is a phenyl ring or an aromatic heterocycle are fluorine, chlorine or bromine atoms or nitro, $C_{1-4}$ alkyl, $C_{1-4}$ alkoxy, methoxycarbonyl, carboxyl, acetyl or nitrile groups. Therefore, especially preferred compounds have the general formula (VIII):

$$R^5-\overset{H}{\underset{H}{C}}=\overset{}{\underset{}{C}}-\overset{\overset{O}{\|}}{C}-\underset{\underset{CH_3}{|}}{N}-\overset{\overset{CO_2CH_3}{|}}{C}=\underset{\underset{OCH_3}{|}}{CH} \qquad (VIII)$$

wherein $R^5$ is an optionally substituted phenyl ring or an optionally substituted heterocycle.

Examples of the compounds of the invention are shown in Table I. Each compound is a single geometric isomer, probably with the following configuration:

$$R^1-\overset{\overset{X}{\|}}{C}-\underset{\underset{R^2}{|}}{N}-\overset{\overset{CO_2R^3}{|}}{C}=\overset{H}{\underset{OR^4}{C}}$$

Evidence for this stereochemical assignment for one particular compound (compound number 1 of Table I) is discussed in Example 1.

TABLE I $$R^1-\overset{\overset{X}{\|}}{C}-\underset{\underset{R^2}{|}}{N}-\overset{\overset{CO_2R^3}{|}}{C}=\underset{\underset{OR^4}{|}}{CH} \qquad (I)$$

| COMPOUND NUMBER | X | $R^1$ | $R^2$ | $R^3$ | $R^4$ | Melting point (°C.) |
|---|---|---|---|---|---|---|
| 1 | O | E-$C_6H_5$CH:CH | $CH_3$ | $CH_3$ | $CH_3$ | Oil |
| 2 | O | E-$C_6H_5$CH:CH | $CH_3$ | $CH_3CH_2$ | $CH_3CH_2$ | Oil |
| 3 | O | E-$C_6H_5$CH:CH | $CH_3$ | $CH_3$ | $CH_3CH_2$ | Oil |
| 4 | O | E-$C_6H_5$CH:CH | $CH_3$ | $CH_3$ | $C_6H_5CH_2$ | 99–100 |
| 5 | O | E-$C_6H_5$CH:CH | $CH_3$ | $C_6H_5CH_2$ | $C_6H_5CH_2$ | Oil |
| 6 | O | E-$C_6H_5$CH:CH | $CH_3$ | $CH_3$ | $CH_3(CH_2)_3$ | Oil |
| 7 | O | E-$C_6H_5$CH:CH | $CH_3$ | $CH_3(CH_2)_3$ | $CH_3(CH_2)_3$ | Oil |
| 8 | O | E-$C_6H_5$CH:CH | $CH_3$ | $C_6H_5CH_2$ | $CH_3(CH_2)_3$ | Oil |
| 9 | O | E-4-Cl—$C_6H_4$CH:CH | $CH_3$ | $CH_3$ | $CH_3$ | 106–108 |
| 10 | O | $C_6H_5CH_2CH_2$ | $CH_3$ | $CH_3$ | $CH_3$ | Oil |
| 11 | O | 4-Cl—$C_6H_4$ | $CH_3$ | $CH_3$ | $CH_3$ | 72–73 |
| 12 | O | 4-$CH_3$O.$C_6H_4$ | $CH_3$ | $CH_3$ | $CH_3$ | Oil |
| 13 | S | E-$C_6H_5$CH:CH | $CH_3$ | $CH_3$ | $CH_3$ | |
| 14 | O | $C_6H_5$C≡C | $CH_3$ | $CH_3$ | $CH_3$ | |
| 15 | O | $C_6H_5CH_2$ | $CH_3$ | $CH_3$ | $CH_3$ | |
| 16 | O | $C_6H_5OCH_2$ | $CH_3$ | $CH_3$ | $CH_3$ | 52–53 |
| 17 | O | E-$C_6H_5$CH:CH | H | $CH_3$ | $CH_3$ | 43–45 |
| 18 | O | E-$C_6H_5$CH:CH | $CH_3CH_2$ | $CH_3$ | $CH_3$ | Oil |
| 19 | O | E-$C_6H_5$CH:CH | $CH_3$ | $CH_3CH_2$ | $CH_3$ | 51–52 |

TABLE I-continued $$\underset{R^2}{\overset{R^1-\underset{\|}{C}-\underset{}{N}-\underset{\overset{}{C}H}{\overset{CO_2R^3}{C}}}{\overset{X}{\|}}}\underset{OR^4}{\sim}$$ (I)

| COMPOUND NUMBER | X | R¹ | R² | R³ | R⁴ | Melting point (°C.) |
|---|---|---|---|---|---|---|
| 20 | O | naphthyl | CH₃ | CH₃ | CH₃ | Oil |
| 21 | O | E-C₆H₅CH:CH | C₆H₅CH₂ | CH₃ | CH₃ | 81–82 |
| 22 | O | E-3-Cl—C₆H₄CH:CH | CH₃ | CH₃ | CH₃ | 102–104 |
| 23 | O | E-C₆H₅CH:C(CH₃) | CH₃ | CH₃ | CH₃ | 79–80 |
| 24 | O | E,E-C₆H₅CH:CHCH:CH | CH₃ | CH₃ | CH₃ | 113–114 |
| 25 | O | E,E-C₆H₅CH:CHCH:CH | CH₃ | CH₃ | C₆H₅CH₂ | 107–108 |
| 26 | O | E-2-Cl—C₆H₄CH:CH | CH₃ | CH₃ | CH₃ | 120–121 |
| 27 | O | E-2-Cl—C₆H₄CH:CH | CH₃ | CH₃ | C₆H₅CH₂ | 103–104 |
| 28 | O | E-(2-furyl)CH:CH | CH₃ | CH₃ | CH₃ | Glass |
| 29 | O | E-C₆H₅CH:CH | C₆H₅ | CH₃ | CH₃ | 82–83 |
| 30 | O | E-(2-thienyl)CH:CH | CH₃ | CH₃ | CH₃ | 64–65 |
| 31 | O | E-(3-pyridyl)CH:CH | CH₃ | CH₃ | CH₃ | |
| 32 | O | H | CH₃ | CH₃ | CH₃ | 51–53 |
| 33 | O | E-(3-thienyl)CH:CH | CH₃ | CH₃ | CH₃ | |
| 34 | O | E-(2-pyridyl)CH:CH | CH₃ | CH₃ | CH₃ | |
| 35 | O | E-(4-pyridyl)CH:CH | CH₃ | CH₃ | CH₃ | |
| 36 | O | E-2,6-di-Cl—C₆H₃CH:CH | CH₃ | CH₃ | CH₃ | Oil |
| 37 | O | E-3,5-di-Cl—C₆H₃CH:CH | CH₃ | CH₃ | CH₃ | |
| 38 | O | E-2,3-di-Cl—C₆H₃CH:CH | CH₃ | CH₃ | CH₃ | |
| 39 | O | E-2,4-di-Cl—C₆H₃CH:CH | CH₃ | CH₃ | CH₃ | |
| 40 | O | E-2,5-di-Cl—C₆H₃CH:CH | CH₃ | CH₃ | CH₃ | |
| 41 | O | E-3,4-di-Cl—C₆H₃CH:CH | CH₃ | CH₃ | CH₃ | |
| 42 | O | E-4-F—C₆H₄CH:CH | CH₃ | CH₃ | CH₃ | |
| 43 | O | E-3-F—C₆H₄CH:CH | CH₃ | CH₃ | CH₃ | |
| 44 | O | E-2-F—C₆H₄CH:CH | CH₃ | CH₃ | CH₃ | |
| 45 | O | E-4-CH₃O—C₆H₄CH:CH | CH₃ | CH₃ | CH₃ | |
| 46 | O | E-3-CH₃O—C₆H₄CH:CH | CH₃ | CH₃ | CH₃ | |
| 47 | O | E-2-CH₃O—C₆H₄CH:CH | CH₃ | CH₃ | CH₃ | |
| 54 | O | E-3-NO₂—C₆H₄CH:CH | CH₃ | CH₃ | CH₃ | |
| 55 | O | E-4-NO₂—C₆H₄CH:CH | CH₃ | CH₃ | CH₃ | |

TABLE I-continued (I)

Structure: R¹—C(=X)—N(R²)—C(CO₂R³)=CH—OR⁴

| COMPOUND NUMBER | X | R¹ | R² | R³ | R⁴ | Melting point (°C.) |
|---|---|---|---|---|---|---|
| 56 | O | E- naphthalen-2-yl-CH:CH | CH₃ | CH₃ | CH₃ | |
| 57 | O | E- naphthalen-1-yl-CH:CH | CH₃ | CH₃ | CH₃ | |

TABLE II: Selected Proton N.M.R. Data.

Table II, below, shows n.m.r. data for selected protons of certain compounds listed in Table I, especially compounds which are oils or glasses. Chemical shifts are measured in p.p.m. from tetramethylsilane using deuterochloroform as solvent. Abbreviations used are:
s=singlet
d=doublet
t=triplet
q=quartet
m=multiplet
br=broad

TABLE II

| COMPOUND NUMBER | DATA |
|---|---|
| 2 | 1.26 and 1.31 (2 overlapping triplets $J$ 7Hz, total 6H), 3.12 (3H,s), 4.17 (centre of 2 overlapping quartets, total 4H), 6.60 (1H,d $J$ 16Hz), 7.50 (1H,s), 7.66 (1H,d $J$ 16Hz). |
| 3 | 1.31 (3H,t $J$ 7Hz), 3.13 (3H,s), 3.77 (3H,s), 4.14 (2H,q $J$ 7Hz), 6.60 (1H,d $J$ 16Hz), 7.53 (1H,s), 7.68 (1H,d $J$ 16Hz). |
| 5 | 3.12 (3H,s), 5.02 (2H,brs), 5.18 (2H,s), 6.49 (1H,d $J$ 16Hz), 7.2–7.35 (15H,m), 7.57 (1H,s), 7.62 (1H,d $J$ 16Hz). |
| 6 | 0.81 (3H,t $J$ 7Hz), 1.1–1.7 (4H,m), 3.12 (3H,s), 3.76 (3H,s), 4.07 (2H,t $J$ 6Hz), 6.60 (1H,d $J$ 16Hz), 7.53 (1H,s), 7.66 (1H,d $J$ 16Hz). |
| 7 | 0.7–0.95 (6H,m), 1.1–1.8 (8H,m), 3.12 (3H,s), 4.08 and 4.17 (2 overlapping triplets, total 4H), 6.61 (1H,d $J$ 16Hz), 7.50 (1H,s), 7.67 (1H,d $J$ 16Hz). |
| 8 | 0.83 (3H,t), 3.13 (3H,s), 5.22 (2H,s), 6.56 (1H,d $J$ 15Hz), 7.53 (1H,s), 7.63 (1H,d $J$ 15Hz). |
| 10 | 2.4 (2H,m), 2.9 (2H,m), 3.01 (3H,s), 3.72 (3H,s), 3.87 (3H,s), 7.34 (1H,s). |
| 12 | 3.12 (3H,s), 3.68 (3H,s), 3.78 (3H,s), 3.80 (3H,s), 6.77 (2H, br d $J$ 8Hz), 7.01 (1H,s), 7.37 (2H, br d $J$ 8Hz). |
| 18 | 1.14 (3H,t $J$ 9Hz), 3.2–3.7 (2H,m), 3.78 (3H,s), 3.91 (3H,s), 6.58 (1H,d $J$ 15Hz), 7.55 (1H,s), 7.68 (1H,d $J$ 15Hz). |
| 20 | 3.19 (3H,s), 3.68 (3H,s), 3.74 (3H,s), 6.99 (1H,s). |
| 28 | 3.07 (3H,s), 3.73 (3H,s), 3.89 (3H,s), 6.38–6.56 (3H,m), 7.32–7.50 (2H,m), 7.44 (1H,s). |
| 36 | 3.11 (3H,s), 3.74 (3H,s), 3.91 (3H,s), 6.73 (1H,d $J$ 16Hz), 7.43 (1H,s), 7.66 (1H, d $J$ 16Hz). |

TABLE II-continued

| COMPOUND NUMBER | DATA |
|---|---|
| | 16Hz). |

The compounds of the invention having the general formula (I) can be prepared from amino acid derivatives of general formula (V) by the steps shown in Scheme I. Throughout Scheme I the terms R¹, R², R³, R⁴ and X are as defined above, and Z is a leaving group such as a halogen atom or an alkoxy group.

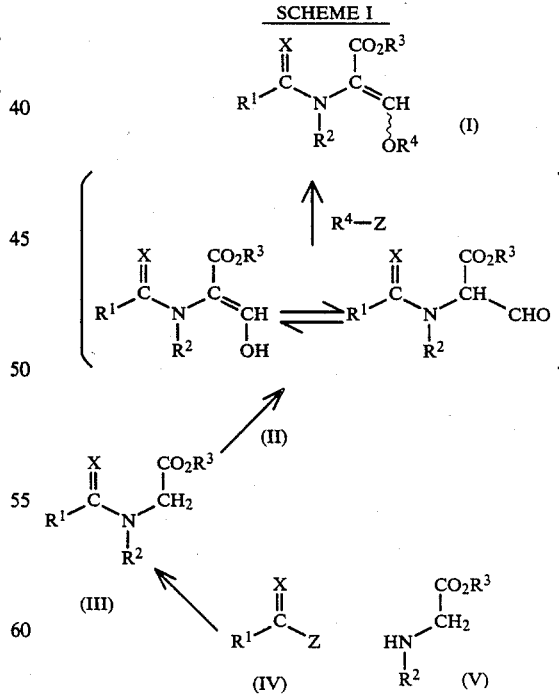

SCHEME I

Thus compounds of general formula (I) in which R³ is not a hydrogen atom can be prepared by treatment of compounds of general formula (II) in which R³ is not a hydrogen atom with a base, such as sodium hydride or potassium carbonate, and a compound of general formula R$^4$-Z, wherein R$^4$ and Z are as defined above, in a suitable solvent such as dimethylformamide.

Compounds of general formula (II) in which R$^3$ is not a hydrogen atom can be prepared by treatment of amino acid derivatives of general formula (III) in which R$^3$ is not a hydrogen atom by treatment with a base, such as sodium hydride, and a formylating agent, such as HCO$_2$R$^3$, wherein R$^3$ (which is not a hydrogen atom) is as defined above, in a suitable solvent such as dimethylformamide.

Compounds of general formula (III) wherein X is an oxygen atom can be prepared by acylating amino acids or their derivatives of general formula (V) with species of general formula (IV) wherein X is an oxygen atom, in the presence of a base if appropriate (use of a base is helpful, for example, if Z is a halogen, such as a chlorine or bromine, atom), in a suitable solvent.

Alternatively, compounds of general formula (III) wherein X is an oxygen atom can be prepared by coupling acids of general formula R$^1$CO$_2$H, wherein R$^1$ is as defined above, with amino acids or their derivatives of general formula (V) in the presence of an appropriate dehydrating reagent or system of reagents.

Compounds of general formula (III) wherein X is a sulphur atom may be prepared from the corresponding compounds of general formula (III) wherein X is an oxygen atom using, for example, 'Lawesson's reagent' (see, for example: S-O. Lawesson et al., *Bull. Soc. Chim. Belg.*, 1978, 87, pages 229 and 525; S. Raucher and P. Klein, *Tet. Letts*, 1980, 31, 4061).

Compounds of general formula (III) wherein R$^3$ is a hydrogen atom can be converted into the corresponding species wherein R$^3$ is not a hydrogen atom by standard esterification procedures.

Compounds of general formulae (IV) and (V) can be prepared by standard methods described in the chemical literature.

SCHEME II $$R^1-\overset{\overset{X}{\|}}{C}-\underset{\underset{R^2}{|}}{N}-\overset{\overset{CO_2R^3}{|}}{C}\underset{OR^4}{\overset{CH}{\diagup}}$$
(I)

↑ −R$^4$OH $$R^1-\overset{\overset{X}{\|}}{C}-\underset{\underset{R^2}{|}}{N}-\overset{\overset{CO_2R^3}{|}}{C}H-CH(OR^4)_2$$
(VI)

↑

$$R^1-\overset{\overset{X}{\|}}{C}-Z \ + \ R^2HN-\overset{\overset{CO_2R^3}{|}}{C}H-CH(OR^4)_2$$
(IV)                 (VII)

An alternative approach to compounds of the invention having the general formula (I) is illustrated by Scheme II. Throughout Scheme II the terms R$^1$,R$^2$,R$^3$,R$^4$,X and Z are as defined above.

Thus compounds of general formula (I) can be prepared from acetals of general formula (VI) by elimination of an alcohol of general formula R$^4$OH under either acidic or basic conditions. An example of a suitable base is lithium di-isopropylamide, and potassium hydrogen sulphate is an example of a suitable acidic reagent (see T Yamada, H Hagiwara and H Uda, *J. Chem. Soc., Chem. Commun.*, 1980, 838, and references therein).

Acetals of general formula (VI) can be prepared by reaction of amines of general formula (VII) with species of general formula (IV) in the presence of a base if appropriate (use of a base is helpful, for example, if Z is a halogen, such as a chlorine or a bromine atom) in a suitable solvent.

Amines of general formula (VII) can be prepared by methods described in the chemical literature (see, for example, 'The Chemistry of Penicillin', Editors H. T. Clarke, J. R. Johnson and R. Robinson, Princeton University Press, 1949, Chapter XVII).

The compounds and metal complexes of the invention are active fungicides, particularly against the diseases:

*Pyricularia oryzae* on rice

*Puccinia recondita, Puccinia striiformis* and other rusts on wheat, *Puccinia hordei, Puccinia striiformis* and other rusts on barley, and rusts on other hosts eg. coffee, pears, apples, peanuts, vegetables and ornamental plants.

*Erysiphe graminis* (powdery mildew) on barley and wheat and other powdery mildews on various hosts such as *Sphaerotheca macularis* on hops

*Sphaerotheca fuliginea* on cucurbits (eg. cucumber), *Podosphaera leucotricha* on apples and *Uncinula necator* on vines.

*Helminthosporium* spp., *Rhynchosporium* spp., *Septoria* spp., *Pseudocercosporella herpotrichoides* and *Gauomannomyces graminis* on cereals.

*Cercospora arachidicola* and *Cercosporidium personata* on peanuts and other *Cercospora* species on other hosts for example sugar beet, bananas, soya beans and rice.

*Botrytis cinerea* (grey mould) on tomatoes, strawberries, vegetables, vines and other hosts.

*Alternaria* species on vegetables (eg. cucumber), oil seed rape, apples, tomatoes and other hosts.

*Venturia inaequalis* (scab) on apples

*Plasmopara viticola* on vines

Other downy mildews such as *Bremia lactucae* on lettuce, *Peronospora* spp. on soybeans, tobacco, onions and other hosts and *Pseudoperonospora humuli* on hops and

*Pseudoperonospora cubensis* on cucurbits

*Phytophthora infestans* on potatoes and tomatoes and other *Phytophthora* spp. on vegetables, strawberries, avocado, pepper, ornamentals, tobacco, cocoa and other hosts.

*Thanatephorus cucumeris* on rice and other *Rhizoctonia* species on various hosts such as wheat and barley, vegetables, cotton and turf.

Some of the compounds have also shown a broad range of activities against fungi *in vitro*. They have activity against various post-harvest diseases of fruit (eg. *Penicillium digitatum* and *italicum* and *Trichoderma viride* on oranges and *Gloesporium musarum* on bananas).

Further some of the compounds are active as seed dressings against *Fusarium* spp., *Septoria* spp., *Tilletia* spp. (bunt, a seed borne disease of wheat), *Ustilago* spp., *Helminthosporium* spp. on cereals, *Rhizoctonia solani* on cotton and *Pyricularia oryzae* on rice.

The compounds can move acropetally in the plant tissue. Moreover, the compounds can be volatile enough to be active in the vapour phase against fungi on the plant.

The compounds may also be useful as industrial (as opposed to agricultural) fungicides, eg. in the prevention of fungal attack on wood, hides, leather and especially paint films.

The compounds may be used as such for fungicidal purposes but are more conveniently formulated into compositions for such usage. The invention thus provides a fungicidal composition comprising a compound of general formula (I) as hereinbefore defined, or a metal complex thereof; and, optionally, a carrier or diluent.

The invention also provides a method of combating fungi, which comprises applying to a plant, to seed of a plant, or to the locus of the plant or seed, a compound or metal complex thereof, as hereinbefore defined.

The compounds and metal complexes of the invention can be applied in a number of ways. For example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hyroponic culture systems. The invention compounds may also be injected into plants or trees and they may also be sprayed onto vegetation using electrodynamic spraying techniques, or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different comositions can be better adapted for various utilities.

The compounds can be used as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or metal complex thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredinet(s) may be used.

The compositions of this invention can comprise also other compound(s) having biological activity, eg. compounds having similar or complementary fungicidal activity or compounds having plant growth regulating, herbicidal or insecticidal activity.

The other fungicidal compound can be, for example, one which is capable of combating ear diseases of cereals (eg. wheat) such as *Septoria, Gibberella* and *Helminthosporium* spp., seed and soil borne diseases and downy and powdery mildews on grapes and powdery mildew and scab on apple etc. These mixtures of fungicides can have a broader spectrum of activity than the compound of general formula (I) alone; further, the other fungicide can have a synergistic effect on the fungicidal activity of the compound of general formula (I). Examples of the other fungicidal compounds are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidione, vinclozolin, penconazole, myclobutanil, R0151297, S3308, pyrazophos, ethirimol, ditalimfos, tridemorph, triforine, nuarimol, triazbutyl, guazatine, propiconazole, prochloraz, flutriafol, chlortriafol ie. the chemical 1-(1,2,4-triazol-1-yl)-2-(2,4-dichlorophenyl)-hexan-2-ol, DPX H6573(1-((bis-4-fluorophenyl)methylsilyl)-methyl)-1H-1,2,4-triazole, triadimefon, triadimenol, diclobutrazol, fenpropimorph, fenpropidine, triademorph, imazalil, fenfuram, carboxin, oxycarboxin, methfuroxam, dodemorph, BAS 454, blasticidin S, Kasugamycin, edifenphos, kitazin P, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarbamate, techlofthalam, bitertanol, bupirimate, etaconazole, streptomycin, cypofuram, biloxazol, quinomethionate, dimethirimol, fenapanil, tolclofos-methyl, pyroxyfur, polyram, maneb, mancozeb, captafol, chlorothalonil, anilazine, thiram, captan, folpet, zineb, propineb, sulphur, dinocap, binapacryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds such as 1-(2-cyano-2-methoxyiminoacetyl)-3-ethyl urea.

The compounds of general formula (I) can be mixed with soil, peat or other rooting media for the protection of plants against seed-borne, soil-borne or foliar fungal diseases.

Suitable insecticides are pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

The plant growth regulating compound can be one which controls weeds or seedhead formation, or selectively controls the growth of the less desirable plants (eg. grasses).

Examples of suitable plant growth regulating compounds, for use with the invention compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluorecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (eg. chlormequat, chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, paclobutrazol, fenpentezol, inabenfide, triapenthenol and tecnazene.

The following Examples illustrate the invention. Throughout these examples, magnesium sulphate was used to dry solutions, reactions involving water-sensitive intermediates were performed under atmospheres of nitrogen, and the following abbreviations are used:
ether=diethyl ether
DMF=N,N-dimethylformamide
s=singlet
m.p.=melting point

EXAMPLE 1

This Example illustrates the preparation of methyl N-cinnamoyl-N-methyl-2-amino-3-methoxypropenoate (Compound number 1 of Table I).

E-Cinnamoyl chloride (34.25 g) was added to a stirred solution of sarcosine (15.21 g) and sodium hydroxide (17.1 g) in water (300 ml). When the exotherm had subsided, the mixture was stirred at room temperature for 4 hours, then washed with several portions of dichloromethane. Acidification with concentrated hydrochloric acid then gave a solid precipitate which was filtered off, washed thoroughly with ether and dried to give E-N-cinnamoylsarcosine (28.91 g, 77% yield) as a free-flowing off-white solid, m.p. 177°–179° C. An analytical sample, crystallised from dichloromethane and petrol, had m.p. 180°–181° C.

The E-N-cinnamoylsarcosine was converted (82% yield) into its methyl ester by refluxing in dry methanol containing a few drops of concentrated sulphuric acid. The product, after triturating with petrol, was a white free-flowing solid, m.p. 56°–58° C. An analytical sample, recrystallised from ethyl acetate and petrol, had m.p. 57°–58° C.

A solution of the methyl ester of E-N-cinnamoylsarcosine (2.03 g) and methyl formate (ca. 11 ml) in dry DMF (15 ml) was added to a stirred suspension of sodium hydride (0.42 g) in dry DMF (20 ml). Only gentle effervescence was observed at first, but after 40 minutes brisk effervescence began [further methyl formate (3 ml) added], subsiding after about 15 minutes and continuing gently until the mixture was carefully diluted with aqueous sodium carbonate after 7.5 hours. The mixture was extracted with ether, and the extracts were washed with aqueous sodium carbonate then water, dried and concentrated under reduced pressure to give recovered E-N-cinnamoylsarcosine methyl ester (0.975 g). The original basic aqueous layer was acidified with concentrated hydrochloric acid and extracted with ether. The extracts were washed with water, dried and concentrated under reduced pressure to give methyl N-cinnamoyl-N-methyl-2-amino-3-hydroxypropenoate (1.108 g, 49% yield, or 94% based on recovered starting material) as a pale red glass, used without further purification for the next step. The proton n.m.r. spectrum recorded using deuteriochloroform as solvent showed duplication of some signals (presumably due to restricted rotation about the amide bond). However, with deuterated dimethylsulphoxide as solvent, the following single set of signals was seen:

delta 2.91 (s,3 protons), 3.61 (s,3 protons), 6.64 (doublet, J 17Hz, 1 proton), 7.3–7.7 (multiplet, 8 protons) ppm.

A solution of methyl N-cinnamoyl-N-methyl-2-amino-3-hydroxypropenoate (1.108 g) in dry DMF (10 ml) was added dropwise to a stirred suspension of sodium hydride (204 mg) in dry DMF (15 ml). When effervescense had subsided (10 minutes), methyl iodide (2.65 ml) was added to the reaction mixture and it was stirred for 1.5 hours at room temperature, then carefully diluted with water and extracted with ether. The extracts were washed successively with aqueous sodium carbonate and water, dried, concentrated under reduced pressure, and chromatographed on a column of silica gel using ether as eluant to give the title compound (0.755 g, 65%) as a viscous colourless oil, better than 99% pure by gas chromatography, and with the following spectroscopic data:

infrared (film): 1712, 1655, 1618 and 1584 (weak) $cm^{-1}$;

$^1$H n.m.r. (CDCl$_3$): delta 3.11 (s,3 protons), 3.76 (s, 3 protons), 3.91 (s, 3 protons), 6.58 (doublet, J 16Hz, 1 proton), 7.3–7.6 (multiplet, 5 protons), 7.46 (s, 1 proton), 7.64 (doublet, J 16Hz, 1 proton) ppm;

$^{13}$C n.m.r. (CDCl$_3$): delta 34.1, 51.2, 62.0, 113.2, 117.3, 127.2, 128.2, 129.0, 134.6, 141.3, 158.1, 164.9, 166.2 ppm.

The data show that the product is a single geometric isomer. The olefinic bond of the cinnamoyl group, derived from E-cinnamoyl chloride, undoubtedly has the E-configuration. The following data suggest that the olefinic bond of the propenoate group has the Z-configuration shown below:

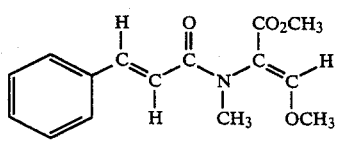

(i) The chemical shift of the olefinic proton on the propenoate group (delta 7.46 ppm.);
(ii) The coupling constant (ca. 1.5Hz) between the nuclei of the ester carbonyl carbon atom and the olefinic hydrogen atom on the propenoate group.

EXAMPLE 2

This Example illustrates the preparation of methyl N-(o-chlorocinnamoyl)-N-methyl-2-amino-3-methoxypropenoate (compound No. 26 of Table I).

A mixture of o-chlorocinnamic acid (6.00 g) and thionyl chloride (ca. 25 ml) was heated under reflux for 2 hours, and then the excess thionyl chloride and other volatile materials were removed under reduced pressure. The residual crude acid chloride, a crystalline compound, as a solution in dry dichloromethane (100 ml), was added dropwise to a stirred solution of sarcosine methyl ester hydrochloride (4.59 g) and triethylamine (10.1 ml) in dry dichloromethane (100 ml). An exothermic reaction took place, and the reaction mixture darkened. After stirring at room temperature for 4 hours, the reaction mixture was filtered. The filtrate was washed successively with dilute hydrochloric acid, aqueous sodium bicarbonate and water, then dried and concentrated to give N-(o-chlorocinnamoyl)-sarcosine methyl ester (8.31 g) as a viscous oil, with a purity of 94% by gas chromatography.

By a procedure analogous to that described in Example 1, part of the crude N-(o-chlorocinnamoyl)sarcosine methyl ester (6.99 g), methyl formate (30 ml) and sodium hydride (2.35 g) gave methyl N-(o-chlorocinnamoyl)-N-methyl-2-amino-3-hydroxypropenoate (4.56 g) as an off-white solid, m.p. 129°–130° C.

Potassium carbonate (3.44 g) and dimethyl sulphate (1.05 ml) were added successively to a stirred solution of -methyl N-(o-chlorocinnamoyl)-N-methyl-2-amino-3-hydroxypropenoate (3.35 g) in dry DMF (25 ml). After 2 hours, the reaction mixture was poured into aqueous sodium bicarbonate and extracted with ether. The extracts were washed with aqueous sodium bicarbonate and water, then dried, concentrated and chromatographed on a column of silica gel using ether as eluant to give the title compound (2.40 g, 40% yield from o-chlorocinnamic acid) as an off-white solid, m.p. 120°–121° C.;

$^1$H NMR (CDCl$_3$): delta 3.10 (3H,s), 3.91 (3H,s), 6.57 (1H, doublet J 17Hz), 7.44 (1H,s), 7.98 (1H, doublet J 17 Hz) ppm

EXAMPLE 3

An emulsifiable concentrate was made up by mixing the ingredients, and stirring the mixture until all the constituents were dissolved.

Compound of Example 1: 10%
Ethylene dichloride: 40%
Calcium dodecylbenzenesulphate: 5%
"Lubrol" L: 10%
"Aromasol" H: 35%

EXAMPLE 4

A composition in the form of grains readily dispersible in a liquid, eg. water, was prepared by grinding together the first three ingredients in the presence of added water and then mixing in the sodium acetate. The resultant mixture was dried and passed through a British Standard mesh sieve, size 44–100, to obtain the desired size of grains.

Compound of Example 1: 50%
"Dispersol" T: 25%
"Lubrol" APN5: 1.5%
Sodium acetate: 23.5%

EXAMPLE 5

The ingredients were all ground together to produce a powder formulation readily dispersible in liquids.
Compound of Example 1: 45%
"Dispersol" T: 5%
"Lissapol" NX: 0.5%
"Cellofas" B600: 2%
Sodium acetate: 47.5%

EXAMPLE 6

The active ingredient was dissolved in a solvent and the resultant liquid was sprayed on to the granules of China clay. The solvent was then allowed to evaporate to produce a granular composition.
Compound of Example 1: 5%
China clay granules: 95%

EXAMPLE 7

A composition suitable for use as a seed dressing was prepared by mixing the three ingredients.
Compound of Example 1: 50%
Mineral oil: 2%
China clay: 48%

EXAMPLE 8

A dusting powder was prepared by mixing the active ingredient with talc.
Compound of Example 1: 5%
Talc: 95%

EXAMPLE 9

A Col formulation was prepared by ball-milling the constituents set out below and then forming an aqueous suspension of the ground mixture with water.
Compound of Example 1: 40%
"Dispersol" T: 10%
"Lubrol" APN5: 1%
Water:

EXAMPLE 10

A dispersible powder formulation was made by mixing together the ingredients set out below and then grinding the mixture until all were thoroughly mixed.
Compound of Example 1: 25%
"Aerosol" OT/B: 2%
"Dispersol" A.C.: 5%
China clay: 28%
Silica: 40%

EXAMPLE 11

This Example illustrates the preparation of a dispersible powder formulation. The ingredients were mixed and the mixture then ground in a comminution mill.
Compound of Example 1: 25%
"Perminal" BX: 1%
"Dispersol" T: 5%
Polyvinylpyrrolidone: 10%
Silica: 25%
China clay: 34%

EXAMPLE 12

The ingredients set out below were formulated into a dispersible powder by mixing then grinding the ingredients.
Compound of Example 1: 25%
"Aerosol" OT/B: 2%
"Dispersol" A: 5%
China clay: 68%

In Examples 3 to 12 the proportions of the ingredients given are by weight.

The compounds set out in Table 1 and numbered 1 to 57 are similarly formulated as specifically described in Examples 3 to 12.

There now follows an explanation of the compositions or substances represented by the various Trade Marks and Trade Names mentioned above.

LUBROL L: a condensate of nonyl phenol (1 mole) with ethylene oxide (13 moles)

AROMASOL H: a solvent mixture of alkylbenzenes

DISPERSOL T & AC: a mixture of sodium sulphate and a condensate of formaldehyde with sodium naphthalene sulphonate LUBROL APN5: a condensate of nonyl phenol (1 mole) with naphthalene oxide (5.5 moles)

CELLOFAS B600: a sodium carboxymethyl cellulose thickener

LISSAPOL NX: a condensate of nonyl phenol (1 mole) with ethylene oxide (8 moles)

AEROSOL OT/B: dioctyl sodium sulphosuccinate

PERMINAL BX: a sodium alkyl naphthalene sulphonate

EXAMPLE 13

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace - 5% of disease on untreated plants
2 = 6–25% of disease on untreated plants
1 = 26–59% of disease on untreated plants
0 = 60–100% of disease on untreated plants
The results are shown in Table III.

TABLE III

| COMPOUND NUMBER | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINES) |
|---|---|---|---|---|---|---|
| 1 | 4 | 4 | 4 | 3 | 4 | 4 |
| 4 | 4 | 3 | 0 | 0 | 4 | 0 |
| 5 | 3 | 3 | 0 | 0 | 4 | 0 |
| 6 | 0 | 0 | 0 | 0 | 3 | 0 |
| 9 | 2 | 4 | 2 | 1 | 4 | 4 |
| 10 | 0 | m | 0 | 0 | 4 | 0 |
| 16 | 0 | 0 | 0 | 0 | 2 | 3 |
| 22 | 4 | 4 | 4 | 3 | 4 | 4 |
| 23 | 0 | 0 | 3 | 0 | 0 | 0 |
| 24 | 0 | 0 | 3 | 0 | 0 | 4 |
| 26 | 4 | 4 | 4 | 4 | 2 | 4 |
| 30 | 3 | 4 | 4 | 0 | m | 4 | m - No data available

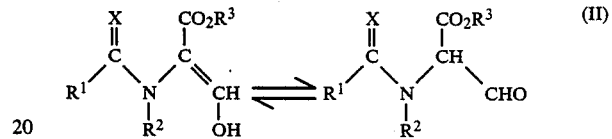  (II)

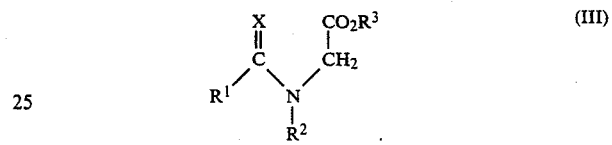  (III)

We claim:

1. Compounds having the formula (I):

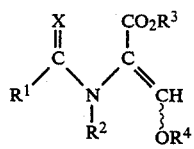  (I)

wherein X, $R^1$, $R^2$ and $R^3$ have the meanings given claim 1.

5. A fungicidal composition comprising a fungicidally effective amount of a compound having the formula (I)

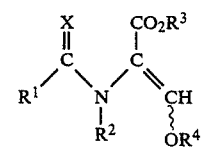  (I)

and stereoisomers thereof, wherein X is an oxygen or a sulphur atom and $R^1$, $R^2$, $R^3$ and $R^4$, which may be the same or different, are alkyl; haloalkyl; cycloalkyl; cycloalkylalkyl; alkenyl which can be substituted by alkyl, cycloalkyl, alkenyl itself substituted by phenyl, naphthyl, phenyl or an aromatic heterocyclic group in which the phenyl and aromatic heterocyclic groups can be substituted by fluorine, chlorine, bromine, nitro, $C_{1-4}$ alkyl, $C_{1-4}$ alkoxy, methoxycarbonyl, carboxyl, acetyl or nitrile; alkynyl which can be substituted by phenyl; phenyl or naphthyl which can be substituted by chlorine or methoxy; benzyl; phenethyl or phenoxymethyl.

2. Compounds having the formula (VIII):

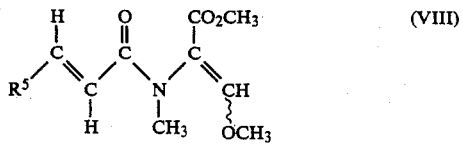  (VIII)

wherein $R^5$ is alkyl; cycloalkyl; alkenyl substituted by phenyl; phenyl or a heterocyclic ring in which the phenyl or heterocyclic ring can be substituted by fluorine, chlorine, bromine, nitro, $C_{1-4}$ alkyl, $C_{1-4}$ alkoxy, methoxycarbonyl, carboxyl, acetyl or nitrile.

3. The compound having the structure:

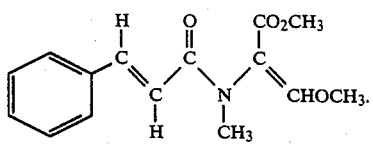

4. Compounds having the formula (II) or (III)

and stereoisomers thereof, wherein X is an oxygen or a sulphur atom; $R^1$, $R^2$ and $R^3$, which may be the same or different, are hydrogen atoms or alkyl; haloalkyl; cycloalkyl; cycloalkylalkyl; alkenyl which can be substituted by alkyl, cycloalkyl, alkenyl which can be substituted by alkyl, cycloalkyl, alkenyl, itself substituted by phenyl, naphthyl, phenyl or an aromatic heterocyclic group in which the phenyl and aromatic heterocyclic groups can be substituted by fluorine, chlorine, bromine, nitro, $C_{1-4}$ alkyl, $C_{1-4}$ alkoxy, methoxycarbonyl, carboxyl, acetyl or nitrile; alkynyl which can be substituted by phenyl; phenyl or naphthyl which can be substituted by chlorine or methoxy; benzyl; phenethyl or phenoxymethyl and $R^4$ can be any of the groups defined for $R^1$, $R^2$ and $R^3$ other than a hydrogen atom; and a carrier therefor.

6. A process for combating fungi which comprises applying to a plant, to seed of a plant, or to the locus of a plant or seed, a fungicidally effective amount of a compound according to claim 1.

7. A process for combating fungi which comprises applying to a plant, to seed of a plant, or to the locus of a plant or seed, a fungicidally effective amount of a composition according to claim 5.

8. A compound according to claim 1 in which $R^3$ and $R^4$ are both methyl.

9. A composition according to claim 5 in which $R^3$ and $R^4$ of compound (I) are both methyl.

* * * * *